United States Patent [19]

Asano et al.

[11] Patent Number: 6,046,164
[45] Date of Patent: Apr. 4, 2000

[54] THERAPEUTIC AGENT FOR DISEASES OF PERIODONTAL TISSUE

[75] Inventors: Taiji Asano, Kyoto; Hajime Sugimoto, Fujieda; Akio Terashima, Kyoto; Yoshiko Nakano, Fujieda; Masahiro Amakawa; Katumasa Saga, both of Kyoto, all of Japan

[73] Assignee: Kaken Pharmaceutical Co., Ltd., Tokyo, Japan

[21] Appl. No.: 08/325,186

[22] PCT Filed: Aug. 25, 1993

[86] PCT No.: PCT/JP93/01211

§ 371 Date: May 24, 1995

§ 102(e) Date: May 24, 1995

[87] PCT Pub. No.: WO95/05840

PCT Pub. Date: Mar. 2, 1995

[51] Int. Cl.⁷ .................................................. A61K 38/00
[52] U.S. Cl. .................................. 514/12; 514/2; 514/21; 530/356; 424/198.1
[58] Field of Search .................... 514/12, 2, 21; 530/356; 424/198.1

[56] References Cited

U.S. PATENT DOCUMENTS 5,158,934  10/1992  Ammann et al. ........................ 514/12
5,368,859  11/1994  Dunn et al. ............................. 424/426
5,372,503  12/1994  Elia ....................................... 433/215
5,397,235   3/1995  Elia ....................................... 433/173
5,405,390   4/1995  O'Leary et al. ......................... 623/16

FOREIGN PATENT DOCUMENTS

WO 93 05823  4/1993  WIPO .
WO 93 10810  6/1993  WIPO .

OTHER PUBLICATIONS

Terranova et al., J. Periodontol, vol. 60, No. 6, 1989, pp. 293–301.
Nakashima, Archs Oral Biol. vol. 37, No. 3, pp. 231–236, 1992.
Cam et al., Int. J. Dev. Bio., vol. 36, No. 3, pp. 381–389, 1992.
Database WPI, Section Ch, Week 9513, Derwent Publications Ltd., London, GB; Class 804, AN 95-093773, XP002046904 & JP 07 017 876 A (Kaken Pharm. Co. Ltd.), Jan. 20, 1995, Abstract.

*Primary Examiner*—Dwayne C. Jones
*Assistant Examiner*—C. Delacroix-Muirheid
*Attorney, Agent, or Firm*—Armstrong, Westerman, Hattori, McLeland and Naughton

[57] ABSTRACT

The present invention relates to a method for treating diseases of periodontal tissue by administering a basic fibroblast growth factor, by which the tissue injury is treated to induce regeneration, curing or new attachment.

13 Claims, 7 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 154
      (B) TYPE: amino acid
      (D) TOPOLOGY: linear (ii) MOLECULE TYPE: protein (xi) SEQUENCE DESCRIPTION: SEQ ID NO:1:

```
Ala Ala Gly Ser Ile Thr Thr Leu Pro Ala Leu Pro Glu Asp Gly Gly
 1               5                  10                  15

Ser Gly Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Ile Lys Leu Gln Leu Gln
50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Asp Glu Cys Phe Phe Phe Glu Arg Leu Glu Ser Asn Asn Tyr Asn
            100                 105                 110

Thr Tyr Arg Ser Arg Lys Tyr Thr Ser Trp Tyr Val Ala Leu Lys Arg
        115                 120                 125

Thr Gly Gln Tyr Lys Leu Gly Ser Lys Thr Gly Pro Gly Gln Lys Ala
130                 135                 140

Ile Leu Phe Leu Pro Met Ser Ala Lys Ser
145                 150
```

(2) INFORMATION FOR SEQ ID NO:2:

(i) SEQUENCE CHARACTERISTICS:
      (A) LENGTH: 153
      (B) TYPE: amino acid
      (D) TOPOLOGY: linear (ii) MOLECULE TYPE: protein (xi) SEQUENCE DESCRIPTION: SEQ ID NO:2:

```
Ala Gly Ser Ile Thr Thr Leu Pro Ala Leu Pro Glu Asp Gly Gly Ser
 1               5                  10                  15

Gly Ala Phe Pro Pro Gly His Phe Lys Asp Pro Lys Arg Leu Tyr Cys
            20                  25                  30

Lys Asn Gly Gly Phe Phe Leu Arg Ile His Pro Asp Gly Arg Val Asp
        35                  40                  45

Gly Val Arg Glu Lys Ser Asp Pro His Ile Lys Leu Gln Leu Gln Ala
50                  55                  60

Glu Glu Arg Gly Val Val Ser Ile Lys Gly Val Cys Ala Asn Arg Tyr
65                  70                  75                  80

Leu Ala Met Lys Glu Asp Gly Arg Leu Leu Ala Ser Lys Cys Val Thr
                85                  90                  95
```

-continued

```
Asp Glu Cys Phe Phe Phe Glu Arg Leu Glu Ser Asn Asn Tyr Asn Thr
            100                 105                 110

Tyr Arg Ser Arg Lys Tyr Thr Ser Trp Tyr Val Ala Leu Lys Arg Thr
            115                 120                 125

Gly Gln Tyr Lys Leu Gly Ser Lys Thr Gly Pro Gly Gln Lys Ala Ile
        130                 135                 140

Leu Phe Leu Pro Met Ser Ala Lys Ser
145                 150
```

THERAPEUTIC AGENT FOR DISEASES OF PERIODONTAL TISSUE

This application is a 371 of PCT/JP93/01211, filed on Aug. 25, 1993.

TECHNICAL FIELD

The present invention relates to a therapeutic agent for diseases of periodontal tissue which comprises a basic fibroblast growth factor as an active principle and a process for treating diseases of periodontal tissue with this agent. More particularly, it relates to an agent and a process used on purpose to treat the disease developed in the periodontal tissue such as periodontal ligament, alveolar bone and cementum to induce regeneration curing (new attachment curing) which is the final object of the treatment.

BACKGROUND OF ARTS

At present, it has been clarified that periodontitis, one of diseases of periodontal tissue is mainly caused by bacteria forming colonies on tooth root surface. As a treatment thereof, main effort is laid on to maintain the periodontal tissue under plaque-free condition by mechanical removing the bacterial plaque adhered to the tooth surface mainly by scaling.

A periodontal surgery applied to serious periodontitis is also performed on purpose to improve environment so as to make oral cleaning more effective, by removing causative factors such as tartar and plaque adhered to a root surface in a periodontal pocket, and pathologic tissue in the same manner as in the above-mentioned therapy. Furthermore, recently chemotherapies with antibiotics are also tried in addition to these therapies.

However, although these therapies remove the pathologic lesion and inhibit progress of the periodontitis, they do not positively repair or regenerate destroyed periodontal tissue. A profile of postoperative curing depends on self healing ability.

Curing forms are classified into regeneration curing (new attachment curing), and reattachment curing. The regeneration curing contains a curing form of cementum morphogenesis wherein collagen fibers are embedded in the postoperatively exposed root surface (new attachment curing) develops with the regeneration of alveolar bone.

On the other hand, the reattachment is a curing containing a long epithelial attachment recognized on the root surface or the accumulation of collagen fibers onto the root surface where a functional recovery can not be desired.

Heretofore, a large number of basic and clinical studies have shown that many forms of postoperative curing forms are reattachment curing. According to histopathological studies, most reattachments are caused by epithelial attachment which formed by the down growth of epithelial cells apically directed from gingival margin, and new attachment is hard to develop.

Particularly, progressed periodontitis is accompanied by complex pocket morphogenesis and various types of osteoclasia, and the bone regeneration is impossible, where the large amount of bone resorption is observed. Melcher (Melcher, A. H.: J. Periodontol., 47, pp 256–260, 1976) has also reported that the proliferation of cells derived from periodontal ligament is necessary to the recovery of the periodontal tissue with the new attachment to the exposed root surface, and that a long junctional epithelium formation, root resorption and ankylosis develop when the cells reaching the root surface are epithelial cells, cells derived from gingiva or cells derived from bone.

From these information, the following subjects have been investigated basically or clinically on purpose to achieve the regeneration curing;

(1) a treatment of the root surface with citratic acid, (2) a local administration of fibronectin, (3) "a guided tissue regeneration method (GTR method)" which inhibits the down growth of epithelial cells using a highly bio-compatible filter and guides the cells derived the periodontal ligament to the root surface, (4) an implantation into a bone-defected site using various implant materials for the resorption of the alveolar bone, and (5) a local administration of Bone Morphogenetic Protein, and the like.

However, they have various problems such as a irritation upon the cells in (1), the stability and antigenicity of fibronectin which is a macromolecule in (2), the necessity of the reoperation for removing of the above-mentioned filter in (3), also complexity of harvest, storage, sterilizing and the ability to be resorbed of the implant material in (4), and easy occurrence of ankylosis in (5). Therefore, the development of an agent for accelerating periodontal tissue regeneration which has safety, easiness of formulation and efficiency is desired.

In the present invention, the purpose is to provide the above-mentioned therapeutic agent for diseases of periodontal tissue which has excellent safety and efficiency, a process for treating diseases of periodontal tissue, an accelerator for fixing osseo-integration between a bone and an implant, and a therapeutic agent for dentin regeneration.

DISCLOSURE OF THE INVENTION

The present invention relates to a therapeutic agent for diseases of periodontal tissue which contains a basic fibroblast growth factor as an active principle.

In consideration of the above-mentioned problems, the inventors found that when an agent containing a basic fibroblast growth factor is used, the agent is excellent in efficiency, safety as a therapeutic agent for diseases of periodontal tissue.

The basic fibroblast growth factor (hereinafter referred to as "bFGF") used in the present invention contains extracts from organs such as hypophysis, brain, retina, corpus leteum, adrenal, kidney, placenta, prostata and thymus; preparations obtained with genetic engineering procedure such as recombinant DNA technique; and muteins which can act as a fibroblast growth factor, in which amino acid(s) is (are) added, other amino acid(s) is (are) substituted for a part of the amino acids, or a part of the amino acids is defected, in the amino acid sequence of the above-mentioned bFGF extracts from the organs or the above-mentioned preparations obtained with genetic engineering procedures such as recombinant DNA technique. These may be used alone or as an admixture thereof.

As the above-mentioned bFGF, for example, the bFGFs described in WO 87/01728 (Translated National Publication No. 500843/1988), WO 89/04832 (Translated National Publication No. 504468/1990), WO 86/07595 (Translated National Publication No. 500036/1988), WO 87/03885 (Translated National Publication No. 501953/1988), European Unexamined Patent Publication No. 237966 (Japanese Unexamined Patent Publication No. 226287/1988), European Unexamined Patent Publication No. 281822 (Japanese Unexamined Patent Publication No. 193/1990), European Unexamined Patent Publication No. 326907 (Japanese Unexamined Patent Publication No. 209894/1990), European Unexamined Patent Publication No. 394951 (Japanese Unexamined Patent Publication No. 61494/1991), European Unexamined Patent Publication No. 493737 (Japanese Unexamined Patent Publication No. 124975/1993) and the like are preferably exemplified.

Among these bFGFs, the polypeptides having the sequence of 154 amino acids of SEQ ID NO. 1 and the sequence of 153 amino acids of SEQ ID No. 2 prepared by the genetic engineering procedure described in U.S. Pat. No. 5,439,818 are particularly preferable from the point of stability and easiness for continuously supplying a required amount of the polypeptide as a material.

Concretely, as described in the Example of U.S. Pat. No. 5,439,818, the polypeptide having the sequence of 154 amino acids of SEQ ID No. 1 is obtained by means of the genetic engineering procedure which comprises preparing a cDNA clone of human basic FGF with bovine 1.4 kb basic subfragment from $\lambda_{gt}$ 10 cDNA library prepared from mRNA of human kidney, constructing an expression vector therefor, and expressing said clone.

"Periodontal tissue" described in the present specification means a peripheral tissue of the tooth, a supporting device of the tooth and a tissue composed of periodontal ligament, alveolar bone, cementum, gingiva and oral mucosa.

"Periodontal ligament" means generally app. 200–250 µm thickness of a connective tissue which connects a tooth with a dental socket and accomplishes a buffer action so as to avoid that the alveolar bone is directly affected by occlusal force and the like. Therefore, in the periodontal ligament, a group of fibers connecting the tooth with the alveolar bone (Sharpey's fibers), and lymph vessels, blood vessels and nerves abundantly distribute, and they supply nutrition to periodontal ligament and protect the tooth and the periodontal tissue from strong occlusal force. As cell components, the periodontal ligament comprises a fibroblast, a cementoblast, an osteoblast and the like.

"Alveolar bone" means a jaw supporting a teeth through the periodontal ligament. The alveolar bone is playing a role as a supporting organ and repeating the remodelling. However, once a balance of the remodelling is lost by diseases of periodontal tissue such as periodontitis, bone resorption is caused with a change of an osteoblast and an osteoclast.

"Cementum" is a bright yellow bone-like connective tissue covering vicinity of the root, and this tissue connects the alveolar bone with the tooth by embedding Sharpey's fibers in the periodontal ligament. The cementum becomes a foreign substance after necrosis and infection by the disappearance of the periodontal ligament because the cementum is supplied with nutrition from the periodontal ligament.

The therapeutic agent for diseases of periodontal tissue of the present invention has an excellent effect for accelerating regeneration of the periodontal tissue such as the above-mentioned cementum, periodontal ligament and alveolar bone. The therapeutic agent of the present invention does not only induce the periodontal tissue regeneration curing (the new attachment curing) which is the final object for the treatment in the above-mentioned periodontal tissue disappeared or injured by progression of periodontitis, but also is effective for the repair of the periodontal tissue after related various diseases such as tooth extraction and enucleation of cyst or oral carcinoma, the acceleration for fixing implants and the regeneration of dentin defected by dental caries. The therapeutic agent of the present invention is used for various treatment of periodontal diseases.

The therapeutic agent for diseases of periodontal tissue of the present invention may be prepared in a form of formulation such as liquid, emulsion, gel, powder, freeze-dried, microcupsule or microsphere, by combining the above-mentioned bFGF with a pharmacologically acceptable additive, for example, a solvent, an isotonicity, an emulsifier, a suspending agent, a stabilizer, or filling material used in the dental field in accordance with general preparation techniques.

Also, sustained release formulation may be prepared according to the object of the present invention.

As a method to have the therapeutic agent for diseases of periodontal tissue included bFGF, a known method, for example, mixing, mixing and kneading, dissolution, immersion, osmosis, spraying, spreading, injection method, or the like is appropriately selected.

When a solvent is used, pH is adjusted to 4.0–8.0, preferably, 4.5–7.0. On the occasion of preparing a formulation, the temperature is controlled to be not more than 30° C., preferably, not more than 15° C.

The bFGF prepared in the above-mentioned formulation may be administrated as a form of external, infusion, cataplasmata and emplastra, liniment, injection, implant formulation, or the like.

The content of the bFGF in the above-mentioned formulation is preferably 0.0001–20% and the amount of the above-mentioned additive(s) to be used except the active principle is preferably 80–99.9999%.

The dosage of the administrated bFGF may be prepared so as to contain 0.1–1000 µg, preferably 1–500 µg.

The therapeutic agent for diseases of periodontal tissue of the present invention may be used by administrating the agent to the part affected by diseases of periodontal tissue, and the root surface, the avulsed gingival surface, the alveolar bone surface or vicinity thereof after the tooth extraction, the pediodontal surgical treatment or the root planing.

The process for treating diseases of periodontal tissue of the present invention is conducted by administrating the bFGF prepared in the above-mentioned formulation to the above affected part or the like, or vicinity thereof in an application form according to the form of administration site, the symptom and the amount to be administrated.

In the process for treating diseases of periodontal tissue of the present invention, the dosage of the above-mentioned therapeutic agent may appropriately be increased or decreased depend on the symptom, the site to be treated. When the bFGF is applied to the affected part or vicinity thereof, in an amount of 0.1–1000 µg a time, preferably 1–500 µg at 1–3 times a day for human, acceleration effect on periodontal tissue regeneration such as alveolar bone, periodontal ligament and the cementum to satisfy the desired therapeutic effect on diseases of periodontal tissue.

BEST MODE FOR CARRYING OUT THE INVENTION

Hereinafter, the present invention is more particularly explained by means of Examples and Comparative Examples, however, the present invention is not limited to the Examples.

The bFGF used in the following tests is the polypeptide having the sequence of 154 amino acids of SEQ ID No. 1 which was prepared with the gene engineering procedure described in WO 87/01728.

FORMULATION EXAMPLE 1

Preparation of a mixture containing the bFGF shown as SEQ ID No. 1

A mixture was prepared by adding a saline to 2.775 mg of the bFGF shown as SEQ ID No. 1 so as to be a total amount of 0.555 ml.

The acceleration action for periodontal tissue regeneration was examined with the above-mentioned mixture containing bFGF. The test method and the results thereof are shown as follows.

EXAMPLE 1 AND COMPARATIVE EXAMPLE 1

Effect of the bFGF on the regeneration after the periodontal tissue defect operation The action of the mixture containing the bFGF shown as SEQ ID No. 1 for each periodontal tissue regeneration after the artificial periodontal tissue defect was histopathologically examined using beagles (n=3).

The normal and healthy periodontal tissue was maintained by the brushing of oral cavity of the beagles and the like. A artificial defect of the periodontal tissue (3 mm in diameter, 2 mm in depth) which reached to the dentin through the alveolar bone and the periodontal ligament from the cheek side bone surface corresponding to the root portion was formed by ablating the mucoperiosteal flap on the upper jaw's right and left anterior tooth part to denude the bone with a conventional method. Further, at the bottom of the defect portion, the dentin was denuded by removing the cementum with a chisel and the like.

Then, after 10 μl of the mixture containing 50 μg of the bFGF shown as SEQ ID No. 1 was administrated by infusing into the right side (Example 1), and 10 μl of the bFGF—free saline was administrated by infusing into the left side (Comparative Example 1) the mucoperiosteal flap was set back to the original position and sutured. The stitches were taken out a week after the operation, and the beagles were killed. Pathogenic specimens were prepared stained with Azan method and observed under an optical microscope.

Figure 1:
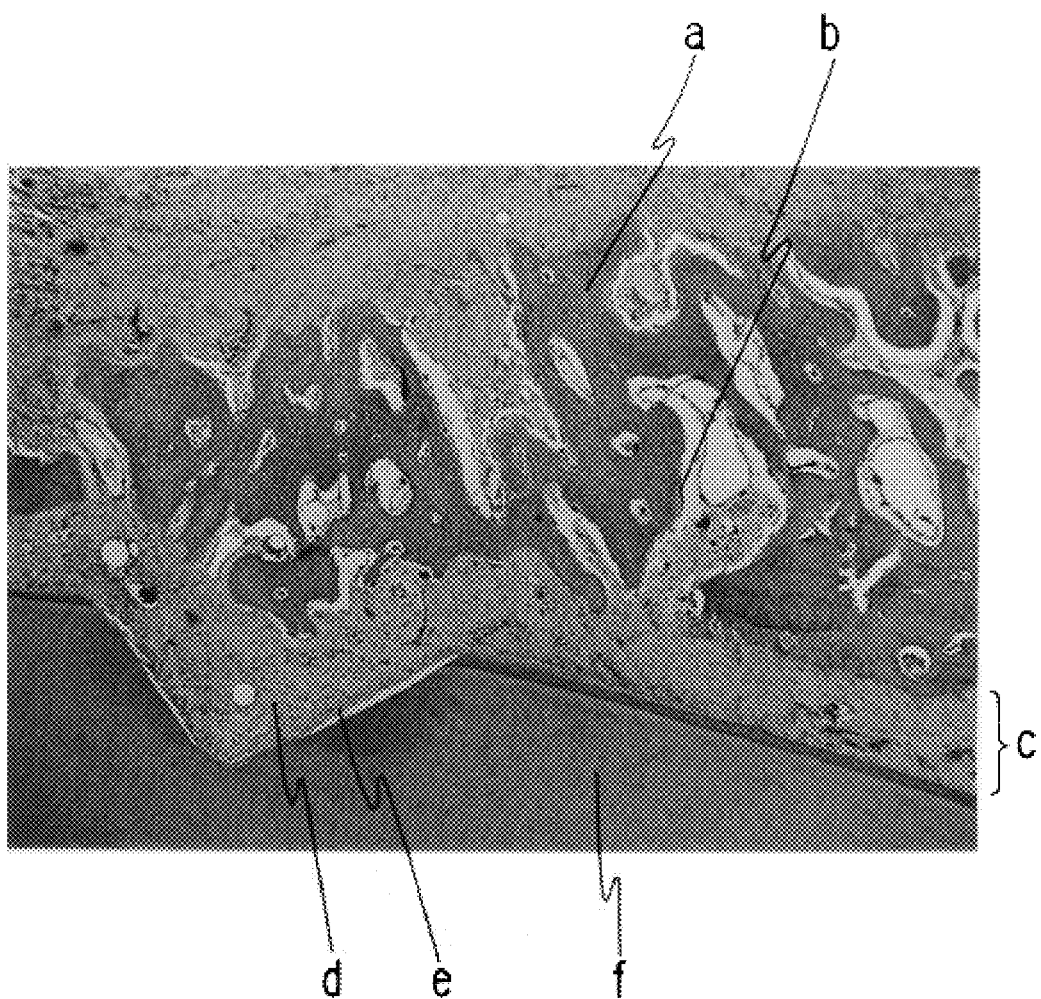
FIG. 1 is an optical microphotograph of pathological specimen of an artificial periodontal tissue defect operation in a dog which was obtained by periodontal tissue regeneration test of Example 1.
Figure 2:
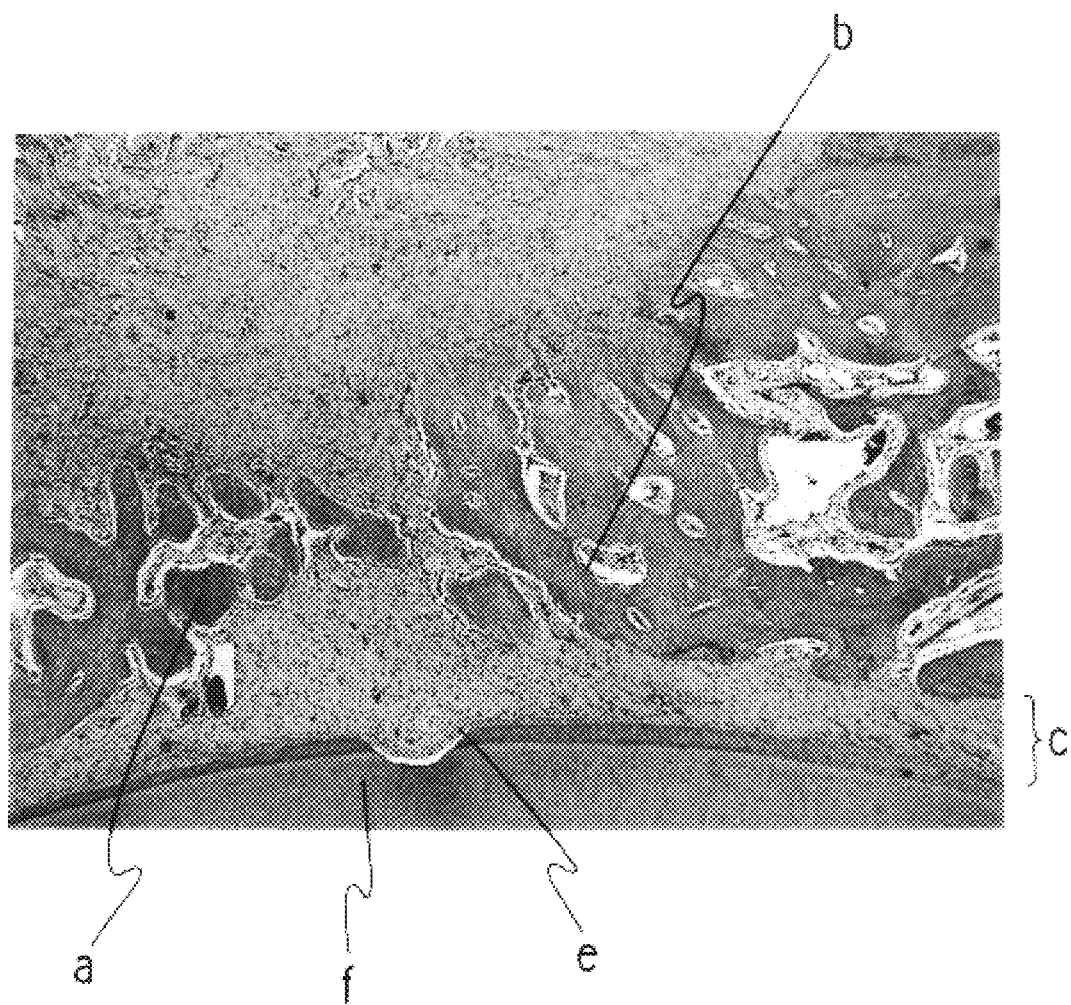
FIG. 2 is an optical microphotograph of pathological specimen of the artificial periodontal tissue defect operation in a dog which was obtained by periodontal tissue regeneration test of Comparative Example 1.

The result of observation in Example 1 is shown in FIG. 1 and the result of observation in Comparative Example 1 is shown in FIG. 2. Each was observed at a 10×magnification.

As shown in FIG. 1, in the specimen of Example 1:

(1) A figure was observed wherein the new alveolar bone a proliferated and irrupted from the section of the alveolar bone on coronal side (the left side of FIG. 1) and the root apex side (the right side of FIG. 1) into the center of the defect cavity. The osteoblasts b were arranged around the trabecular bone, and the osteoclasts were also recognized. A tendency of active remodelling in the bone was found.

(2) A figure was observed wherein the formation of new periodontal ligament c between the new alveolar bone and the root surface was wide in width in comparison with the existing periodontal ligament and abundant with capillary vessels, the fibers (Sharpey's fibers) d were running and began to be arranged obliquely or vertically against the root surface and embedded in the new cementum e.

(3) The new cementum e was formed on the root surface which was denuded from the surface of the existing cementum, and almost uniformly formed also in the resorption lacuna of the dentin on the root surface.

The new periodontal ligament c between the new alveolar bone a and the root surface represented the figure similar to that of the existing periodontal ligament.

On the contrary, as shown in FIG. 2, in Comparative Example 1:

(4) In the same manner as in Example 1, a figure was observed wherein the new alveolar bone a on which the osteoblasts b were arranged around the trabecular bone from the section of the alveolar bone on the coronal side (the left side of FIG. 2) and the root apex side (the right side of FIG. 2), proliferated and irrupted into the center of the defect cavity. However, the degree of the new bone formation was lower than that in Example 1.

(5) The proliferation degree of fibers in the new periodontal ligament c generated between the new alveolar bone a and the root surface was also low.

(6) Although the new cementum e was also formed from the surface of the existing cementum onto the root surface, the thickness decreases as getting toward the center of the defect cavity. The degree of formation thereof was lower than that in Example 1.

(7) Formation of the long junctional epithelial attachment by the irrupting of inner marginal epithelium, root resorption and ankylosis were recognized in neither Example 1 nor Comparative Example 1.

As is clear from these results, because the regeneration or the repair of the periodontal tissue is more remarkably recognized in Example 1 wherein the bFGF shown as SEQ ID No. 1 was applied to the tissue in spite of the bigger defect in Example 1 compared with that in Comparative Example 1, it was found that the bFGF shown as SEQ ID No. 1 has an obviously preferable acceleration action to the regeneration of the destroyed periodontal tissue, i.e. the destroyed periodontal ligament, alveolar bone, cementum and the like, and is useful for the treatment of diseases of periodontal tissue.

FORMULATION EXAMPLE 2

Preparation of fibrin gel containing the bFGF shown as SEQ ID No. 1

The gel was prepared so as to be 1.77 mg/ml of the bFGF shown as SEQ ID No. 1, 41.6 mg/ml of fibrinogen (available from Behringwerk), 0.41 mg/ml of aprotinin (available from Behringwerk) and 33.3 U/ml of thrombin (available from Behringwerk) in 0.1 M phosphate buffer (pH 6.5).

EXAMPLE 2 AND COMPARATIVE EXAMPLE 2

Acceleration action for periodontal tissue regeneration of the bFGF

The action of the fibrin gel containing the bFGF shown as SEQ ID No. 1 for each periodontal tissue regeneration after the artificial periodontal tissue defect operation was histopathologically examined using beagles (n=3).

The beagles used in the experiment were maintained under the condition of normal healthy periodontal tissue by the brushing and the like. The extraction of the fourth premolars of lower jaw was carried out under systemic anesthesia with pentobarbital (available from Nacalai tesque Co., Ltd.) and local anesthesia with Xylocaine (available from Fujisawa Pharmaceutical Co., Ltd.). One month later, the extraction cavity was healed, and abnormality was not recognized in the oral cavity. Then both of the third premolars of the lower jaw were used as experimental portions. The mucoperiosteal flaps were ablated under systemic anesthesia and infiltration anesthesia of the experimental portion to denude the bone. Three wall artificial bone defect (3 mm of the width of buccal-to-lingual×3 mm of the mesiodistal width×4 mm of the depth) was prepared in the distal portion of the third premolars and, then the cementum on the denuded root surface was thoroughly removed with a chisel or the like to denude the dentin. The left side (Comparative Example 2) was filled with 28.25 μl of the fibrin gel without the bFGF shown as SEQ ID No. 1, and the right side (Example 2) was filled with 28.25 μl of the fibrin gel containing 50 μg of the bFGF shown as SEQ ID No. 1. Then, the mucoperiosteal flap was set back to the original position and sutured. Two and four weeks after the operation, the beagles were killed, and pathogenic tissue specimens were prepared in accordance with a conventional manner and observed under an optical microscope.

Figure 3:
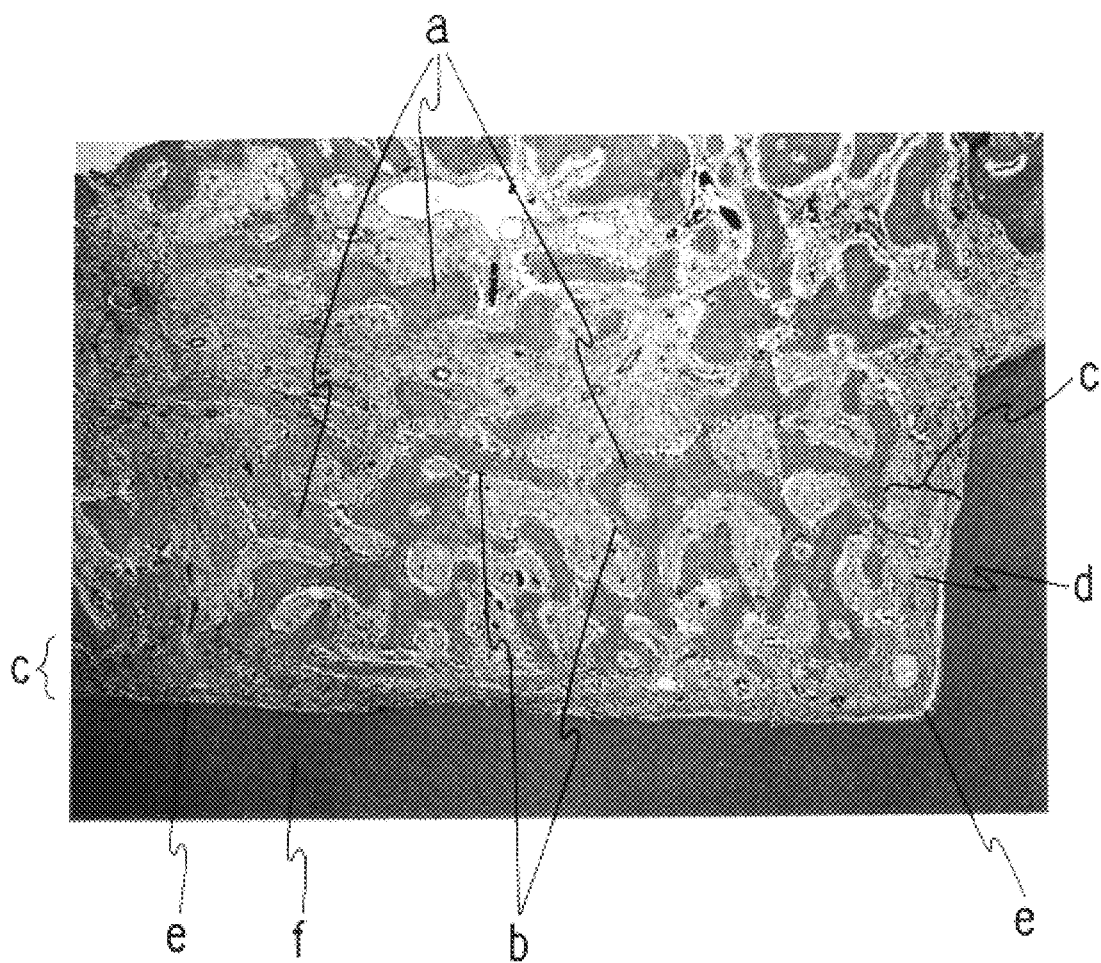
FIG. 3 is an optical microphotograph of pathological specimen two weeks after the artificial periodontal tissue defect operation in a dog which was obtained by periodontal tissue regeneration test of Example 2.
Figure 4:
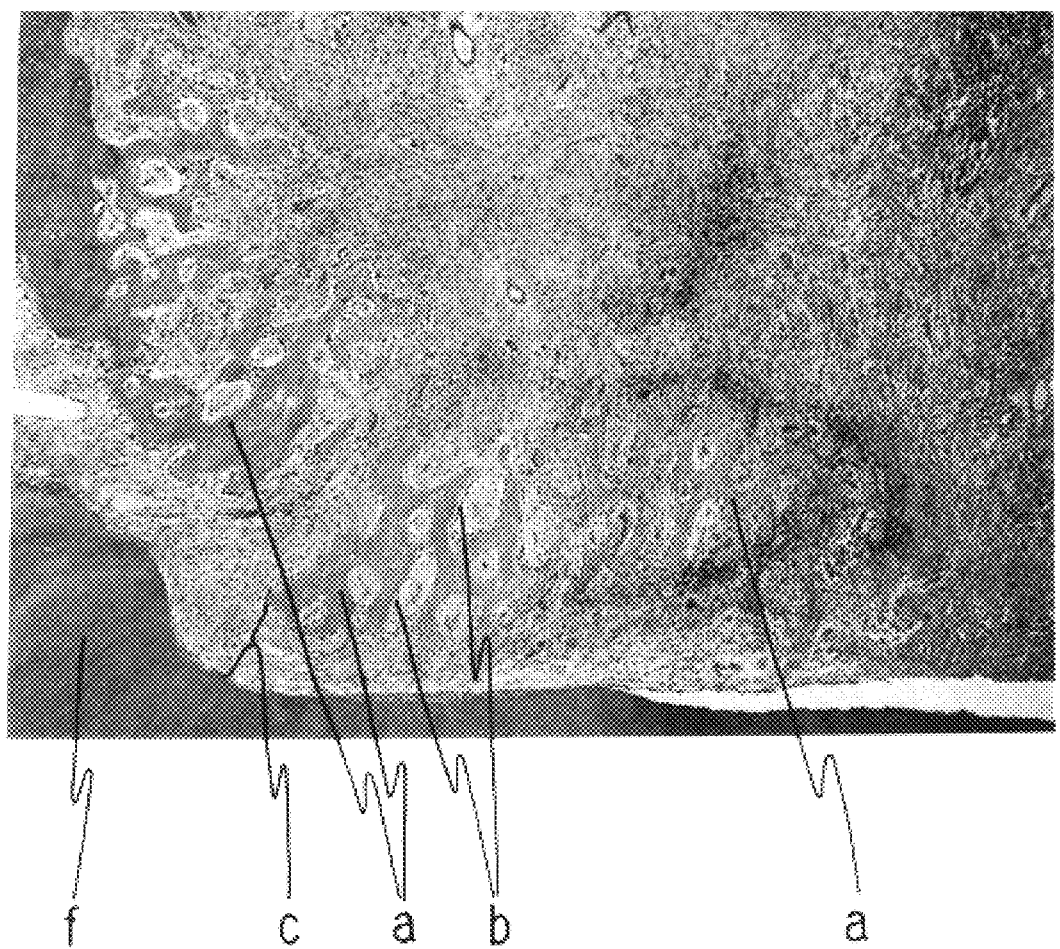
FIG. 4 is an optical microphotograph of pathological specimen two weeks after the artificial periodontal tissue operation in a dog which was obtained by periodontal tissue regeneration test of Comparative Example 2.
Figure 5:
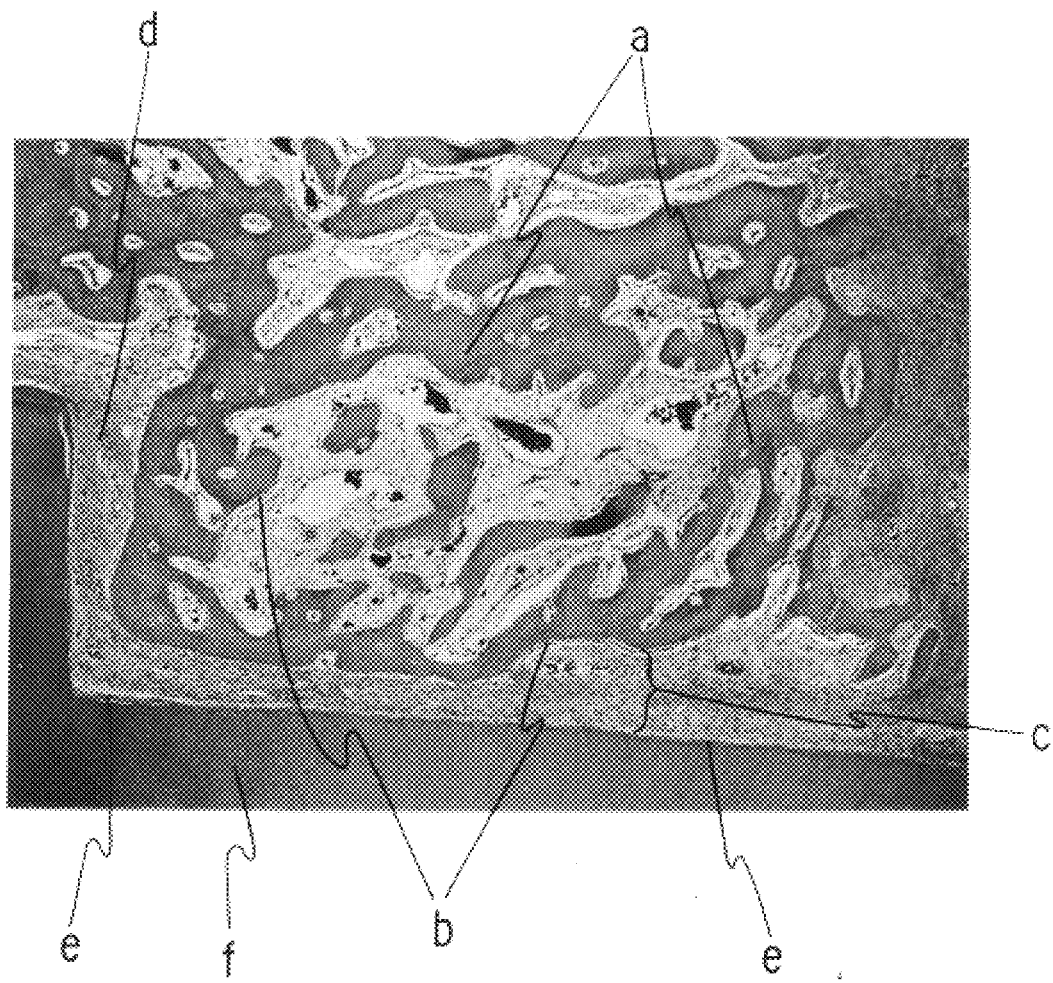
FIG. 5 is an optical microphotograph of pathological specimen four weeks after the artificial periodontal tissue operation in a dog which was obtained by periodontal tissue regeneration test of Example 2.
Figure 6:
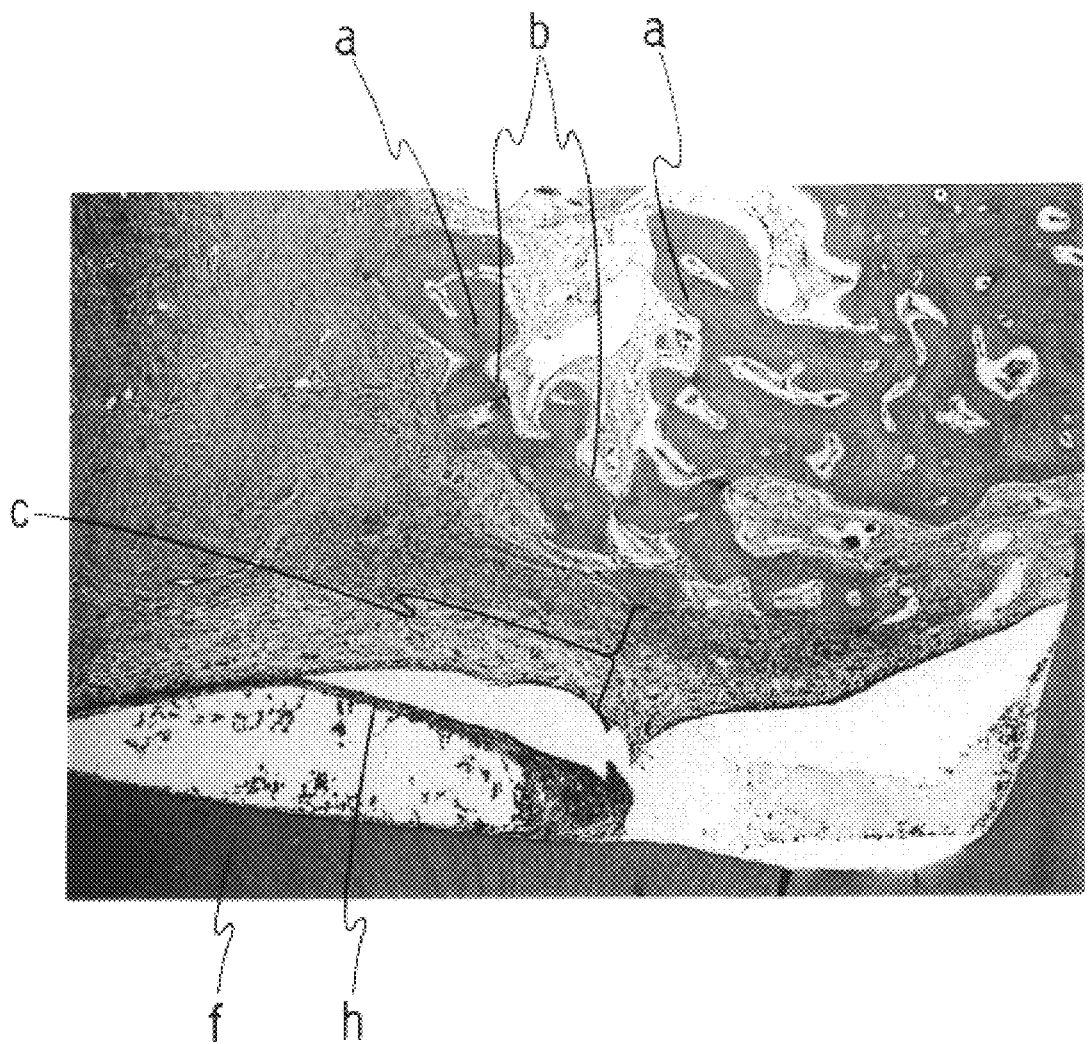
FIG. 6 is an optical microphotograph of pathological specimen 4 weeks after the artificial periodontal tissue operation in a dog which was obtained by periodontal tissue regeneration test of Comparative Example 2.
Figure 7:
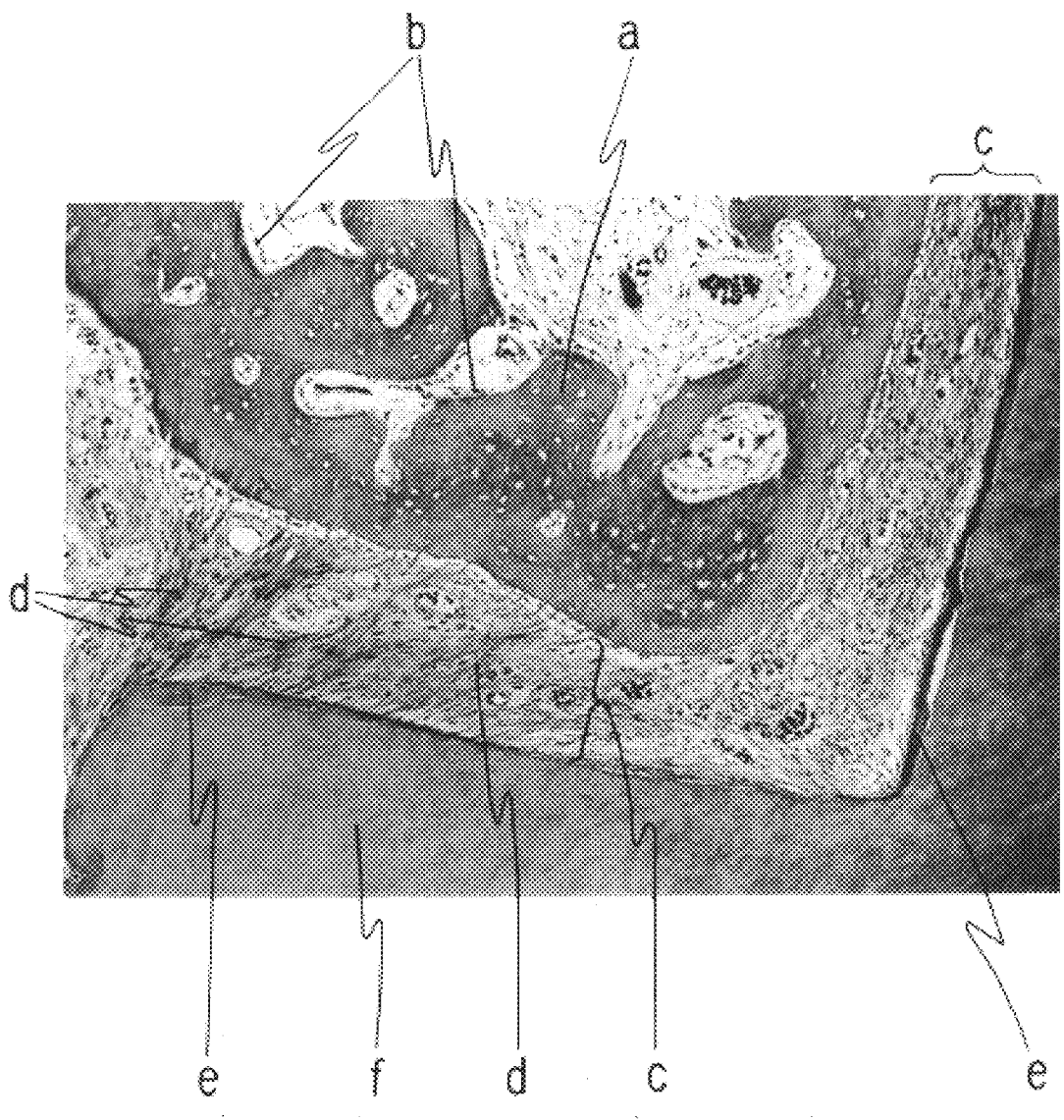
FIG. 7 is a magnified optical microphotograph of a part of pathological specimen 4 weeks after the artificial periodontal tissue operation in a dog which was obtained by periodontal tissue regeneration test of Example 2.

The results of the optical microscopic observation of the pathogenic specimens in Example 2 are shown in FIG. 3, 5 and 7, and the results of the optical microscopic observation of the pathogenic specimens in Comparative Example 2 are shown in FIG. 4 and 6. The results 2 weeks after the operation are shown in FIG. 3 and 4, the results 4 weeks after the operation are shown in FIG. 5, 6 and 7. FIG. 3–6 show the specimens stained with hematoxylin-eosin and observed with a 10×magnification, FIG. 7 shows a part of FIG. 5 stained with Azan and was observed under a 25×magnification.

As shown in FIG. 3, in the specimen 2 weeks after the operation of Example 2:

(1) The marked hyperplasia of coral-like new alveolar bone a was found from the bone sectioned surface on the root apex side (the right side of FIG. 3) toward the coronal side (the left side of FIG. 3) in the defect cavity. The osteoblasts b were arranged around the trabecular bone, and the osteoclasts were also recognized.

(2) The new periodontal ligament c between the new alveolar bone a and the root surface from the root apex toward the coronal side is abundant with capillary vessels, the fibers d were running and arranged in parallel with the root surface. Particularly the periodontal ligament close to the bone section was well grown and the portion was found wherein the fibers were obliquely running on the root surface.

(3) In one case, a figure was recognized wherein the neo cementum e was formed on the root surface denuded from the surface of the existing cementum.

On the contrary, as shown in FIG. 4, in the specimen 2 weeks after the operation in Comparative Example 2:

(4) Although the hyperplasia of the new alveolar bone a was recognized from the bone sectioned surface on the root apex side (the left side of FIG. 4) toward the coronal side (the right side of FIG. 4) in the defect cavity in the same manner as in Example 2, the degree of the formation of the new alveolar bone was low and there was a fibrous connective tissue which is abundant with cell components between the narrow trabecular bones.

(5) The degree of the hyperplasia of fibers in the new periodontal ligament c was low and the fasciculi was thin.

(6) No case was recognized wherein the new cementum was formed.

As shown in FIGS. 5 and 7, in the specimen 4 weeks after the operation in Example 2:

(1) The proliferating tendency of the new alveolar bone a from the root apex side (the left side of FIG. 5, the down side of FIG. 7) was further enhanced compared with the proliferation in 2 weeks after the operation, and active remodelling was recognized and filled the major part of the bone defect.

(2) A figure was observed wherein the new periodontal ligament c between the new alveolar bone a and the root surface further matured, the fibers d were increased and began to be arranged obliquely or vertically against the root surface. The fibers being turned Sharpey's fibers, were embedded in the new cementum e. The figure was similar to that of the existing periodontal ligament.

(3) In all cases, the new cementum e was formed on the root surface which was denuded from the surface of the existing cementum. The new cementum e was almost uniformly formed in the resorption cavity of the dentin of the root surface expressed. The thickness thereof increased compared with that of the cementum in the specimen 2 weeks after the operation.

On the contrary, as shown in FIG. 6, in the specimen 4 weeks after the operation in Comparative Example 2:

(4) Although the remodelling of the new alveolar was recognized compared with the tissue in 2 weeks after the operation in Comparative Example 2, the amount of the newly formed alveolar bone occupying the defect was yet smaller compared with that in Example 2.

(5) The degree of the new periodontal ligament c was similar to that in the specimen 2 weeks after the operation of Comparative Example 2, the density of the fibers in the new periodontal ligament c was low. There were many fasciculi being thin.

(6) Although the new cementum e was formed from the existing cementum surface onto the root surface, the degree of the amount of the newly formed cementum was smaller compared with that in Example 2.

(7) The formation of the long junctional epithelium h by irrupting the inner marginal epithelium was recognized in one case.

(8) Root resorption and ankylosis were not recognized in both Example 2 and Comparative Example 2.

The results obtained from these observations are shown in Table 1. Pathological findings were displayed as evaluation points (group value) and statistically treated with WILCOXON test (one-sided test). As is clear from FIGS. 3–7 and Table 1, the acceleration effect to the periodontal tissue regeneration of the bFGF shown as SEQ ID No. 1 came to be recognized obviously with regard to the alveolar bone regeneration 2 weeks after the operation and to be more remarkable with regard to regeneration of the periodontal ligament and cementum 4 weeks after the operation.

According to the above results, it has been revealed that the bFGF has important role for the treatment of diseases of periodontal tissue, by which amelioration of the periodontal tissue being destroyed and injured is remarkably accelerated.

Namely, according to the present invention, there can be provided the therapeutic agent for diseases of periodontal tissue which can be applied to the regeneration curing into a condition appropriately maintaining the balance of the disappeared periodontal tissue by progression of periodontitis, i.e., the whole tissue of cementum, periodontal ligament and alveolar bone and the like, and also applied to the repair of periodontal tissue after the tooth extraction and the enucleation of cystic or the oral carcinoma, the acceleration for fixing implants, the regeneration of dentin defected by dental caries, and the like. Further, the process for treating diseases of periodontal tissue using the agent which has no side effect and a high effect is established.

TABLE 1

| Finding | Example 2 (medication group) | | Comparative Example 2 (non-medication group) | |
| --- | --- | --- | --- | --- |
| | Evaluation (point) | Average ± Standard deviation | Evaluation (point) | Average ± Standard deviation |
| Two weeks after operation | | | | |
| Alveolar bone: | | | | |
| new | 3,2,2 | 2.3 ± 0.58* | 1,1,1 | 1 ± 0 |
| bone density | 1,2,2 | 1.7 ± 0.58* | 0.5,1,1 | 0.8 ± 0.29 |
| Periodontal ligament regeneration | 2,0.5,0.5 | 1 ± 0.87* | 0.5,0.5,0 | 03 ± 0.29 |
| Cementum: regeneration | 2,0,0, | 0.7 ± 1.15* | 0.5,0,0 | 0.2 ± 0.29 |
| Four weeks after operation | | | | |
| Alveolar bone: | | | | |
| new | 3,2,3 | 2.7 ± 0.58* | 0.5,2,2 | 1.5 ± 0.87 |
| bone density | 2,3,3 | 2.7 ± 0.58* | 1,2,2 | 1.7 ± 0.58 |
| Periodontal ligament regeneration | 2,2,2 | 2 ± 0* | 0.5,0.5,0.5 | 0.5 ± 0 |
| Cementum: regeneration | 2,2,2, | 2 ± 0* | 0.5,1,0.5 | 0.67 ± 0.29 |

*: $P < 0.05$ (compared with control group)
Evaluation (point): No(0), very slight (0.5), slight (1), moderate (2), remarkable (3)

EXAMPLE 3

Safety of the bFGF for Organisms

The safety of active principle in the present invention was examined as to the bFGF shown as SEQ ID No. 1. On the single dose toxicity test, each $LD_{50}$ value of the bFGF shown as SEQ ID No. 1 by subcutaneous and oral administrations to the male and female rats was not less than 75 mg/kg. The $LD_{50}$ value of the bFGF shown as SEQ ID No. 1 by subcutaneous and oral administrations to the male and female dogs were not less than 5 and 3.36 mg/kg, respectively. As described above, administrable maximum dose was given for rats and dogs. However, no death case was recognized on both male and female.

INDUSTRIAL AVAILABILITY

According to the present invention, a therapeutic agent and process for diseases of periodontal tissue which has an excellent regeneration action to periodontal tissue, an accelerator for fixing an implant and a therapeutic agent for dentin regeneration can be provided with the bFGF.

What is claimed is:

1. A method for treating diseases of periodontal tissue comprising administering to a subject in need of such treatment a therapeutically effective amount of a basic fibroblast growth factor alone or in combination with one or more pharmacologically suitable carriers or diluents wherein said basic fibroblast growth factor comprises 0.1 to 1000 μg and is a polypeptide selected from the group consisting of SEQ ID No.: 1 and SEQ ID No. 2.

2. The method according to claim 1 wherein the periodontal tissue is selected from the group consisting of periodontal ligament, alveolar bone and cementum or mixtures thereof.

3. The method according to claim 2 wherein the periodontal tissue is periodontal ligament.

4. The method according to claim 2 wherein the periodontal tissue is alveolar bone.

5. The method according to claim 2 wherein the periodontal tissue is cementum.

6. The method according to claim 1 wherein the basic fibroblast growth factor is a purified recombinant protein.

7. The method according to claim 1 wherein regeneration curing of periodontal tissue is induced.

8. The method according to claim 1 wherein new attachment curing of periodontal tissue is induced.

9. The method according to claim 1 comprising 1 to 500 μg of said basic fibroblasts growth factor.

10. The method according to claim 9 wherein said basic fibroblast growth factor is administered 1 to 3 times a day.

11. The method according to claim 1 wherein said basic fibroblast growth factor is administered 1 to 3 times a day.

12. A method for accelerating the fixation of osseointegration between a bone and an implant comprising administering to a subject in need of such treatment a therapeutically effective amount of a basic fibroblast growth factor alone or in combination with one or more pharmacologically suitable carriers or diluents wherein said basic fibroblast growth factor comprises 0.1 to 1000 μg and is a polypeptide selected from the group consisting of SEQ ID NO:1 and SEQ ID NO:2.

13. A method for dentin regeneration comprising administering to a subject in need of such treatment a therapeutically effective amount of a basic fibroblast growth factor alone or in combination with one or more pharmacologically suitable carriers or diluents wherein said basic fibroblast growth factor comprises 0.1 to 1000 μg and is a polypeptide selected from the group consisting of SEQ ID NO:1 and SEQ ID NO:2.

* * * * *